US007365179B2

(12) United States Patent
Brenner

(10) Patent No.: US 7,365,179 B2
(45) Date of Patent: Apr. 29, 2008

(54) MULTIPLEXED ANALYTICAL PLATFORM

(75) Inventor: Sydney Brenner, Cambridge (GB)

(73) Assignee: Compass Genetics, LLC, Lutherville, MD (US)

( * ) Notice: Subject to any disclaimer, the term of this patent is extended or adjusted under 35 U.S.C. 154(b) by 408 days.

(21) Appl. No.: 10/934,617

(22) Filed: Sep. 2, 2004

(65) Prior Publication Data

US 2005/0059065 A1    Mar. 17, 2005

Related U.S. Application Data

(60) Provisional application No. 60/543,887, filed on Feb. 12, 2004, provisional application No. 60/501,273, filed on Sep. 9, 2003.

(51) Int. Cl.
C12N 15/11    (2006.01)
C07H 21/04    (2006.01)

(52) U.S. Cl. .................................. 536/23.1; 536/24.3

(58) Field of Classification Search ............... None
See application file for complete search history.

(56) References Cited

U.S. PATENT DOCUMENTS

| | | | |
|---|---|---|---|
| 4,293,652 A | 10/1981 | Cohen ........................ 435/91.1 |
| 4,321,365 A | 3/1982 | Wu et al. ................... 536/24.2 |
| 5,093,245 A | 3/1992 | Keith et al. ................ 435/91.2 |
| 5,102,785 A | 4/1992 | Livak et al. .................... 435/6 |
| 5,149,625 A | 9/1992 | Church et al. ................. 435/6 |
| 5,424,186 A | 6/1995 | Fodor et al. .................... 435/6 |
| 5,445,934 A | 8/1995 | Fodor et al. .................... 435/6 |
| 5,503,980 A | 4/1996 | Cantor ............................ 435/6 |
| 5,508,169 A | 4/1996 | Deugau et al. ................. 435/6 |
| 5,565,324 A | 10/1996 | Still et al. ....................... 435/6 |
| 5,599,921 A | 2/1997 | Sorge et al. .............. 536/24.33 |
| 5,631,134 A | 5/1997 | Cantor ............................ 435/6 |
| 5,635,400 A | 6/1997 | Brenner .................... 435/301.1 |
| 5,714,330 A | 2/1998 | Brenner et al. ................. 435/6 |
| 5,723,598 A | 3/1998 | Lerner et al. ............... 536/25.3 |
| 5,744,305 A | 4/1998 | Fodor et al. .................... 435/6 |
| 5,763,175 A | 6/1998 | Brenner .......................... 435/6 |
| 5,770,358 A | 6/1998 | Dower et al. ................... 435/6 |
| 5,846,719 A | 12/1998 | Brenner et al. ................. 435/6 |
| 5,916,810 A | 6/1999 | Jarvik ......................... 435/440 |
| 5,935,793 A | 8/1999 | Wong ............................. 435/6 |
| 5,981,176 A | 11/1999 | Wallace ......................... 435/6 |
| 6,007,987 A | 12/1999 | Cantor et al. ................... 435/6 |
| 6,013,445 A | 1/2000 | Albrecht et al. ................ 435/6 |
| 6,023,540 A | 2/2000 | Walt et al. ..................... 385/12 |
| 6,054,270 A | 4/2000 | Southern ........................ 435/6 |
| 6,060,596 A | 5/2000 | Lerner et al. ............... 536/25.3 |
| 6,103,474 A | 8/2000 | Dellinger et al. ............... 435/6 |
| 6,124,092 A | 9/2000 | O'Neill et al. ................. 435/6 |
| 6,171,797 B1 | 1/2001 | Perbost ........................... 435/6 |
| 6,280,950 B1 | 8/2001 | Lipshutz et al. ................ 435/6 |
| 6,287,778 B1 | 9/2001 | Huang ............................ 435/6 |
| 6,323,043 B1 | 11/2001 | Caren et al. .................. 436/518 |
| 6,346,423 B1 | 2/2002 | Schembri ..................... 436/518 |
| 6,348,313 B1 | 2/2002 | Sibson ............................ 435/6 |
| 6,355,431 B1 | 3/2002 | Chee et al. ..................... 435/6 |
| 6,355,432 B1 | 3/2002 | Fodor et al. .................... 435/6 |
| 6,406,848 B1 | 6/2002 | Bridgham et al. .............. 435/6 |
| 6,440,667 B1 | 8/2002 | Fodor et al. .................... 435/6 |
| 6,440,677 B2 | 8/2002 | Lipshutz et al. ................ 435/6 |
| 6,458,530 B1 | 10/2002 | Morris et al. .................. 435/6 |
| 6,514,699 B1 | 2/2003 | O'Neill et al. ................. 435/6 |
| 6,544,739 B1 | 4/2003 | Fodor et al. .................... 435/6 |
| 6,573,338 B2 | 6/2003 | Halverson et al. ........... 525/375 |
| 6,632,641 B1 | 10/2003 | Brennan et al. ............ 435/91.2 |
| 2003/0003490 A1 | 1/2003 | Fan et al. ....................... 435/6 |
| 2003/0049616 A1 | 3/2003 | Brenner et al. ................. 435/6 |
| 2003/0104436 A1 | 6/2003 | Morris et al. .................. 435/6 |
| 2004/0086914 A1 | 5/2004 | Cole et al. ...................... 435/6 |
| 2004/0132056 A1 | 7/2004 | Su .................................. 435/6 |
| 2004/0146901 A1 | 7/2004 | Morris et al. .................. 435/6 |
| 2004/0259118 A1* | 12/2004 | Macevicz ....................... 435/6 |

OTHER PUBLICATIONS

Brenner, et al, "In vitro cloning of complex mixtures of DNA on microbeads: Physical separation of differentially expressed cDNAs," Proc. Natl. Acad. Sci., 97: 1665-1670 (2000).

Brenner, et al, "Gene Expression Analysis by Massively Parallel Signature Sequencing (MPSS) On Microbead Arrays", Nature Biotechnology (2000) 18:630-634.

Czarnik, A. W., "Encoding Methods for Combinatorial Chemistry", Current Opinion in Chemical Biology (1997) 1:60-66.

(Continued)

Primary Examiner—James Martinell
(74) Attorney, Agent, or Firm—David C. Scherer; Carol L. Francis; Bozicevic, Field & Francis LLP

(57) ABSTRACT

The invention provides a system and reagents for carrying out multiplexed analytical measurements using the hybridization of oligonucleotide tags to addressable solid phase supports to obtain simultaneous readouts from hundreds to tens of thousands of reactions. In one aspect of the invention, analyte interaction moieties, such as oligonucleotide probes, are produced that are each labeled with a unique synthesis tag constructed from a set of two-nucleotide "words." During or after an assay, the synthesis tags are converted to hybridization tags that are used in the readout step. Hybridization tags are constructed to maximize discrimination in the readout. Hybridization tags of the invention are preferably constructed from oligonucleotide "words" selected from a minimally cross-hybridizing set using combinatorial synthesis techniques. In a further aspect, discrimination in the readout is enhanced by employing hybridization tags that are constructed with words having the "comma-less" property and by minimizing or eliminating extraneous nucleic acids associated with the hybridization tag during a readout step.

6 Claims, 8 Drawing Sheets

OTHER PUBLICATIONS

Fan, et al., "Parallel Genotyping of Human SNPs Using Generic High-density Oligonucleotide Tag Arrays", Genome Research (2000) 10:853-860.

Fan, et al, " A Versatile Assay for High-Throughput Gene Expression Profiling on Universal Array Matrices", Genome Research (2004) 14:878-885.

Gerry, et al, "Universal DNA Microarray Method for Multiplex Detection of Low Abundance Point Mutations", J. Mol. Biol. (1999) 292:251-262.

Gronostajski, R.M., "Site-specific DNA Binding of Nuclear Factor I: Effect of the Spacer Region", Nucleic Acids Research (1987) 15:5545-5559.

Hirschhorn, et al, "SBE-TAGS: An Array-based Method for Efficient Single-Nucleotide Polymorphism Genotyping", Proc. Natl. Acad. Sci. (2000) 97:12164-12169.

Hughes, et al, "Expression Profiling Using Microarrays Fabricated by an Ink-jet Oligonucleotide Synthesizer", Nature Biotechnology (2001) 19:342-347.

Weiler and Hoheisel, "Combining the preparation of oligonucleotide arrays and synthesis of high-quality primers," Anal. Biochem., 243: 218-227 (1996).

Brenner and Lerner, "Encoded combinatorial chemistry," Proc. Natl. Acad. Sci., 89: 5381-5383 (1992).

* cited by examiner

Combinatorial Tag With No "Commas"

Combinatorial Tag With "Commas" Between Words

Combinatorial Tag With "Commas" at Each End

Combinatorial Tag With "Commas-less" Property

|       |       |       |       |       | Melting Temperatue | | |
|-------|-------|-------|-------|-------|-------|-------|-------|
|       |       |       |       |       | Basic | Salt Adjusted | Nearest Neighbor |
| gtcta | tgtca | cttgt | tcitt | acaga | 53 | 61 | 52 |
|       |       |       |       |       |    |    |    |
| tgtca | tgtca | cttgt | tcitt | acaga | 53 | 61 | 54 |
| acaga | tgtca | cttgt | tcitt | acaga | 53 | 61 | 54 |
| cagaa | tgtca | cttgt | tcitt | acaga | 53 | 61 | 53 |
| aicat | tgtca | cttgt | tcitt | acaga | 51 | 59 | 52 |
| gaact | tgtca | cttgt | tcitt | acaga | 53 | 61 | 53 |
| cttgt | tgtca | cttgt | tcitt | acaga | 53 | 61 | 53 |
| tcitt | tgtca | cttgt | tcitt | acaga | 51 | 59 | 52 |
|       |       |       |       |       |    |    |    |
| gtcta | gtcta | cttgt | tcitt | acaga | 53 | 61 | 52 |
| gtcta | acaga | cttgt | tcitt | acaga | 53 | 61 | 52 |
| gtcta | cagaa | cttgt | tcitt | acaga | 53 | 61 | 52 |
| gtcta | aicat | cttgt | tcitt | acaga | 51 | 59 | 51 |
| gtcta | gaact | cttgt | tcitt | acaga | 53 | 61 | 53 |
| gtcta | cttgt | cttgt | tcitt | acaga | 53 | 61 | 52 |
| gtcta | tcitt | cttgt | tcitt | acaga | 51 | 59 | 51 |
|       |       |       |       |       |    |    |    |
| gtcta | tgtca | gtcta | tcitt | acaga | 53 | 61 | 52 |
| gtcta | tgtca | tgtca | tcitt | acaga | 53 | 61 | 52 |
| gtcta | tgtca | acaga | tcitt | acaga | 53 | 61 | 52 |
| gtcta | tgtca | cagaa | tcitt | acaga | 53 | 61 | 52 |
| gtcta | tgtca | aicat | tcitt | acaga | 51 | 59 | 51 |
| gtcta | tgtca | gaact | tcitt | acaga | 53 | 61 | 53 |
| gtcta | tgtca | tcitt | tcitt | acaga | 51 | 59 | 51 |
|       |       |       |       |       |    |    |    |
| gtcta | tgtca | cttgt | gtcta | acaga | 54 | 63 | 54 |
| gtcta | tgtca | cttgt | tgtca | acaga | 54 | 63 | 54 |
| gtcta | tgtca | cttgt | acaga | acaga | 54 | 63 | 54 |
| gtcta | tgtca | cttgt | cagaa | acaga | 54 | 63 | 54 |
| gtcta | tgtca | cttgt | aicat | acaga | 53 | 61 | 52 |
| gtcta | tgtca | cttgt | gaact | acaga | 54 | 63 | 54 |
| gtcta | tgtca | cttgt | cttgt | acaga | 54 | 63 | 54 |
|       |       |       |       |       |    |    |    |
|       |       |       | Mean  |       | 53 | 61 | 53 |
|       |       |       | Std Dev |     | 1  | 1  | 1  |

Fig. 4

MULTIPLEXED ANALYTICAL PLATFORM

This application claims priority in U.S. provisional applications Ser. No. 60/501,273 filed 9 Sep. 2003 and Ser. No. 60/543,887 filed 12 Feb. 2004, each of which is incorporated herein by reference in its entirety.

FIELD OF THE INVENTION

The invention relates generally to systems for carrying out highly multiplexed analytical measurements, and more particularly, to compositions and methods for providing readouts of multiplexed analytical reactions with oligonucleotide tags.

BACKGROUND

Many scientific and commercial endeavors, particularly in genetics and drug discovery, require rapid and efficient analysis of large sets of molecules, such as libraries of organic compounds, complementary DNAs (cDNAs), genomic fragments, and the like. For example, in genetics, unraveling the genetic basis of complex traits remains an unsolved problem of immense medical and economic importance. One approach to this problem is to carry out trait-association studies in which a large set of genetic markers from populations of affected and unaffected individuals are compared. Such studies depend on the non-random segregation, or linkage disequilibrium, between the genetic markers and genes involved in the trait or disease being studied. Unfortunately, the extent and distribution of linkage disequilibrium between regions of the human genome is not well understood, but it is currently believed that successful trait-association studies in humans would require the measurement of 30-50,000 markers per individual in populations of at least 300-400 affected individuals and an equal number of controls, Kruglyak and Nickerson, Nature Genetics, 27: 234-236 (2001); Lai, Genome Research, 11: 927-929 (2001); Risch and Merikangas, Science, 273: 1516-1517 (1996); Cardon and Bell, Nature Reviews Genetics, 2: 91-99 (2001). The cost of such studies using current technology is staggering, Weaver, Trends in Genetics, pgs. 36-41 (December, 2000).

In the area of drug discovery, business imperatives and advances in biotechnology, such as the availability of genomic sequences, high throughput gene expression analysis, proteomics, and bioinformatics, have created a need for efficient large-scale methods for identifying potential drug targets, validating targets, and identifying lead compounds, e.g. Myers and Baker, Nature Biotechnology, 19: 727-730 (2001). Such methods should have the capability to analyze simultaneously tens of thousands of compounds, or more, with minimal handling. For example, it is estimated that there are between 30-35,000 genes in the human genome and that as many as thirty-five percent of expressed genes appear in multiple forms due to alternative transcript splicing or other post-transcriptional processing events, e.g. Mironov et al, Genome Research, 9: 1288-1293 (1999) (alternative splicing); Beaudoing et al, Genome Research, 10: 1001-1010 (2000)(variant polyadenylation). Moreover, proteins expressed from such gene products are subject to a wide variety of post-translational modifications, e.g. Han et al, Int. J. Biochem., 24: 19-28 (1992). Even if only a few dozen of these gene products are eventually are identified as validated targets for a particular disease, lead compounds must still be selected from many hundreds of thousands candidate molecules, followed by lead optimization.

In the pharmaceutical, chemical and biotechnical fields, molecular tagging strategies have been proposed as a means for efficiently analyzing large numbers of analytes in a single assay reaction, e.g. Brenner, U.S. Pat. No. 5,763,175 (DNA sequencing); Lerner et al, U.S. Pat. No. 6,060,596 (combinatorial libraries); Giese, U.S. Pat. No. 5,360,819 (chemical analysis); Church et al, U.S. Pat. No. 4,942,124 (DNA sequencing); Sill et al, U.S. Pat. No. 5,565,324 (combinatorial libraries); Southern et al, U.S. Pat. No. 6,218,111 (mass tag labels for oligonucleotides) Van Ness et al, U.S. Pat. No. 6,312,893 (mass tags for genotyping); Schoemaker et al, European Pat. Publ. EP 0799897A1 (tracking yeast mutants); Fan et al, PCT publ. WO 00/58516 (genotyping); Wolber et al, U.S. Pat. No. 6,235,483 (labeling cDNAs); Taylor et al, Biotechniques, 30: 661-669 (2000)("fluid" arrays); and the like. In most approaches, an analytical reaction is followed by a readout that involves spatial separation of the molecular tags, for example, by mass spectrometry, electrophoresis, hybridization to solid phase supports, or the like. A common difficulty of large-scale tagging approaches is associating a particular tag with a particular analyte or reaction. The only exception is the method of Brenner (U.S. Pat. No. 5,763,175) which attaches tags to polynucleotide analytes by sampling procedure and does not require the identity of the tags for a readout. The usual approach is to prepare each tag and its corresponding analyte interacting moiety, e.g. a locus-specific primer, or the like, in a separate batch reaction and then to mix the conjugates prior to a multiplexed assay, e.g. Fan et al, Genome Research, 10: 853-860 (2000); Chen et al, Genome Research, 10: 549-557 (2000); and the like. This is a serious impediment to the efficient large-scale use of tags in multiplexed analyses.

In some systems, tags have been synthesized by combinatorial methods in order to efficiently generate large sets, e.g. Lerner et al (cited above); Dower et al, U.S. Pat. No. 5,770,358; and Brenner et al U.S. Pat. No. 5,763,175. However, such systems require that selected subsets of tags be individually decoded so that the analytes of interest can be identified. In Brenner's system, the decoding is accomplished by hybridizing copies of the tags to an array of tag complements. Even though individual "words" making up the tags are minimally cross-hybridizing, the tags as a whole are capable of forming spurious duplexes with unintended complements when an N-word tag forms a perfectly match duplex with N-1 consecutive words of a complement. Such spurious duplexes could be avoided by using tags consisting of "words" that make up a so-called "comma-less" code, e.g. Crick et al, Proc. Natl. Acad. Sci., 43: 416-421 (1957).

In view of the above, many fields, such as medical and industrial genetics, drug discovery, and the like, would benefit by the availability of a versatile high throughput platform for carrying out a multitude of different analytical assays. In particular, many advantages would accrue from a tag-based analytical platform that (i) provided analytical reagents using existing microarray technology, (ii) employed a common microarray-based readout, (iii) permitted the simultaneous synthesis of large numbers of tag-analyte interaction moieties in the same reaction, and (iv) used combinatorial tags made of words having the "comma-less" property. Such advantages include the economies of high volume production, use of the widespread expertise in microarray technology, and use of the installed base of microarray analyzers.

SUMMARY OF THE INVENTION

The present invention includes a system and reagents for carrying out multiplexed analytical measurements using the hybridization of oligonucleotide tags to addressable solid phase supports to obtain simultaneous readouts from hundreds to tens of thousands of reactions. Reagents for use in the system are efficiently produced using microarray fabrication techniques. In one aspect of the invention, using such techniques, analyte interaction moieties are produced that are each labeled with a unique synthesis tag constructed from a set of two-nucleotide "words." After fabrication, the synthesis tags are converted to hybridization tags that are used in the readout step. Preferably, synthesis tags are as short as possible to minimize the occurrence of spurious tags due to synthesis errors. On the other hand, hybridization tags are constructed to maximize discrimination in the readout. In another aspect of the invention, the hybridization tags of the invention are constructed from oligonucleotide "words" selected from a minimally cross-hybridizing set using combinatorial synthesis techniques. Discrimination in the readout may be further enhanced by employing hybridization tags that are constructed with words having the "comma-less" property and by minimizing or eliminating extraneous nucleic acids associated with the hybridization tag during a readout step.

The invention provides important efficiencies in the large-scale production of analyte interaction moieties, particularly oligonucleotide probes for genotyping.

BRIEF DESCRIPTION OF THE DRAWINGS

FIG. 4 lists melting temperatures of selected tags consisting of four words each having the comma-less property.

Definitions

Figure 1A:
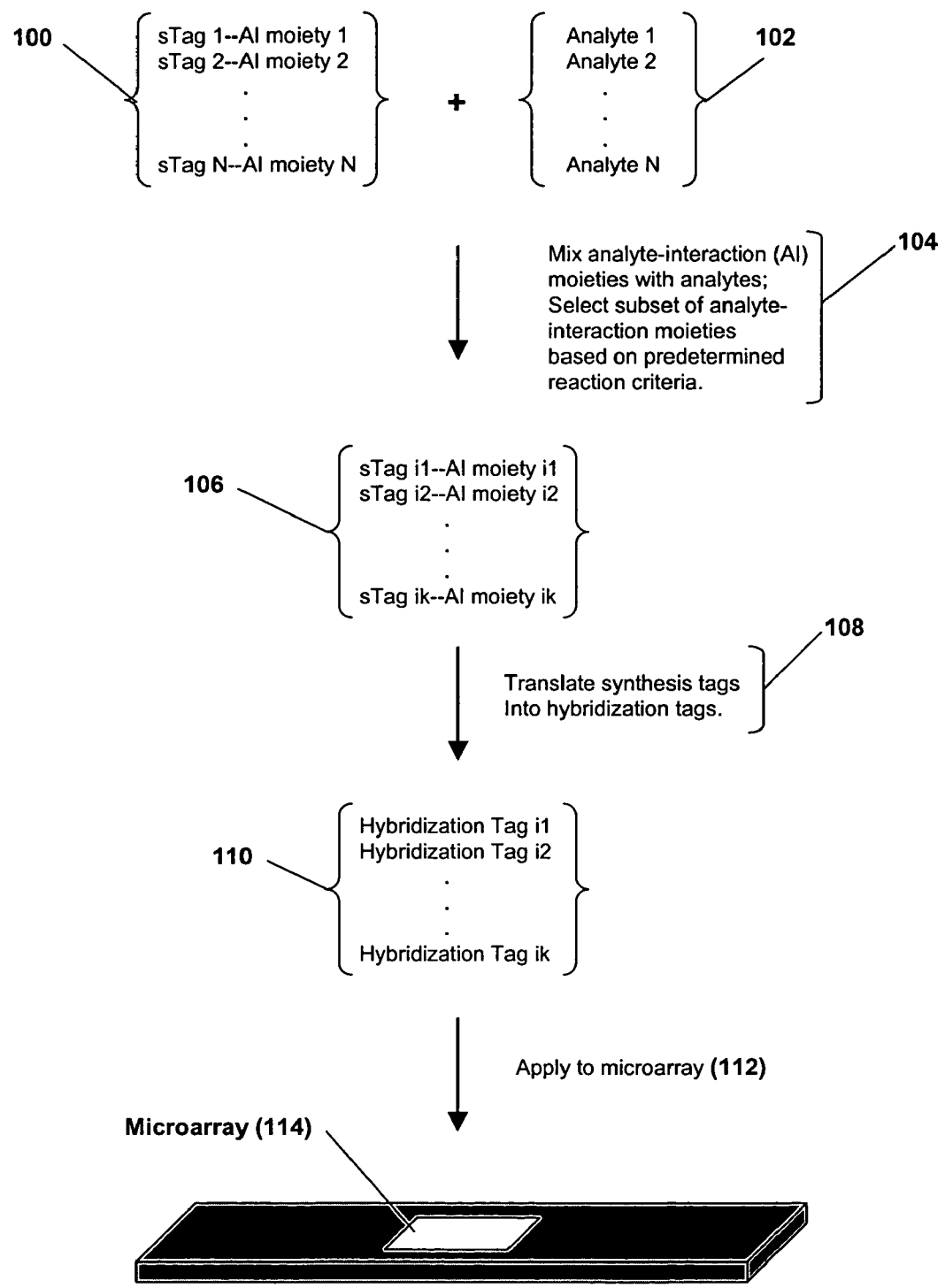
FIG. 1A diagrammatically illustrates the method of analyzing a plurality of analytes in accordance with one aspect of the invention in which synthesis tags are decoded after a multiplexed analytical reaction.

"Complement" or "tag complement" as used herein in reference to oligonucleotide tags refers to an oligonucleotide to which an oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleotides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine. Unless otherwise noted the terminology and atom numbering conventions will follow those disclosed in Strachan and Read, Human Molecular Genetics 2 (Wiley-Liss, New York, 1999). Usually oligonucleotides of the invention comprise natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the only proviso that they are capable of specific hybridization. Such analogs include synthetic nucleosides designed to enhance binding properties, reduce complexity, increase specificity, and the like. Oligonucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of oligonucleotides for use with the invention that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, oligonucleotides containing C-5 propynylpyrimidines, and like compounds. Such oligonucleotides are either available commercially or may be synthesized using methods described in the literature.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identity, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)-(not C)-C-(not C)-C . . . " and the like.

As used herein "signature sequence" means a sequence of nucleotides derived from a polynucleotide such that the ordering of nucleotides in the signature is the same as their ordering in the polynucleotide and the sequence contains sufficient information to identify the polynucleotide in a population. Signature sequences may consist of a segment of consecutive nucleotides (such as, (a,c,g,t,c) of the polynucleotide "acgtcggaaatc"), or it may consist of a sequence of every second nucleotide (such as, (c,t,g,a,a,) of the polynucleotide "acgtcggaaatc"), or it may consist of a sequence of nucleotide changes (such as, (a,c,g,t,c,g,a,t,c) of the polynucleotide "acgtcggaaatc"), or like sequences.

As used herein, the term "complexity" in reference to a population of polynucleotides means the number of different species of polynucleotide present in the population.

As used herein, "amplicon" means the product of an amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced in a polymerase chain reaction (PCR), by replication in a cloning vector, or by linear amplification by an RNA polymerase, such as T7 or SP6, or by like techniques.

As used herein, "addressable" in reference to tag complements means that the nucleotide sequence, or perhaps other physical or chemical characteristics, of a tag complement can be determined from its address, i.e. a one-to-one correspondence between the sequence or other property of the tag complement and a spatial location on, or characteristic of, the solid phase support to which it is attached. Preferably, an address of a tag complement is a spatial location, e.g. the planar coordinates of a particular region containing copies of the tag complement. However, tag complements may be addressed in other ways too, e.g. by microparticle size, shape, color, frequency of micro-transponder, or the like, e.g. Chandler et al, PCT publication WO 97/14028.

As used herein, "ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically.

As used herein, "microarray" refers to a solid phase support, which may be planar or a collection of microparticles, that carries or carry oligo- or polynucleotides fixed or immobilized, usually covalently, at specific addressable locations. Preferably, a microarray is a solid phase support having a planar surface, which carries an array of nucleic acids, each member of the array comprising identical copies of an oligonucleotide or polynucleotide immobilized to a fixed region, which does not overlap with those of other members of the array. Typically, the oligonucleotides or polynucleotides are single stranded and are covalently attached to the solid phase support at known, determinable, or addressable, locations. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999).

As used herein, "genetic locus," or "locus" in reference to a genome or target polynucleotide, means a contiguous subregion or segment of the genome or target polynucleotide. As used herein, genetic locus, or locus, may refer to the position of a gene or portion of a gene in a genome, or it may refer to any contiguous portion of genomic sequence whether or not it is within, or associated with, a gene. Preferably, a genetic locus refers to any portion of genomic sequence from a few tens of nucleotides, e.g. 10-30, in length to a few hundred nucleotides, e.g. 100-300, in length.

As used herein, "sequence marker" means a portion of nucleotide sequence at a genetic locus. A sequence marker may or may not contain one or more single nucleotide polymorphisms, or other types of sequence variation, relative to a reference or control sequence. In accordance with the invention, a sequence marker may be interrogated by specific hybridization of an isostringency probe.

As used herein, "allele frequency" in reference to a genetic locus, a sequence marker, or the site of a nucleotide means the frequency of occurrence of a sequence or nucleotide at such genetic loci or the frequency of occurrence of such sequence marker, with respect to a population of individuals. In some contexts, an allele frequency may also refer to the frequency of sequences not identical to, or exactly complementary to, a reference sequence.

As used herein, "uniform" in reference to spacing or distribution means that a spacing between objects, such as sequence markers, or events may be approximated by an exponential random variable, e.g. Ross, Introduction to Probability Models, $7^{th}$ edition (Academic Press, New York, 2000). In regard to spacing of sequence markers in a mammalian genome, it is understood that there are significant regions of repetitive sequence DNA in which a random sequence model of the genomic DNA does not hold. "Uniform" in reference to spacing of sequence markers preferably refers to spacing in uniques sequence regions, i.e. non-repetitive sequence regions, of a genome.

As used herein, "analyte" means any molecule, including organic, inorganic, or biomolecule, whose presence or absence or quantity or concentration in a sample is to be determined in an assay. In particular, biomolecule analytes include oligonucleotides, polynucleotides, genomic fragments, messenger RNAs (mRNAs), proteins, antibodies, enzymes, complementary DNAs (cDNAs), and like compounds. Preferably, analytes of the invention are oligo- or polynucleotides, such as genomic fragments, cDNAs, mRNAs, and the like.

As used herein, the term "readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

DETAILED DESCRIPTION OF THE INVENTION

The present invention provides a system and methods for carrying out multiplexed analytical reactions, particularly for detecting single nucleotide polymorphisms. Important aspects of the invention include efficient large-scale synthesis of tag-analyte interaction moieties for polynucleotide analytes using in situ microarray synthesis techniques, "comma-less" hybridization tags for improved discrimination in complex hybridization reactions, using short synthesis tags in the large-scale production of tag-analyte interaction moieties followed by "error-free" conversion into longer hybridization tags to minimize the effects of errors in in situ synthesis, and use of reagents of the invention for large-scale genotyping and other analytical reactions.

Figure 1B:
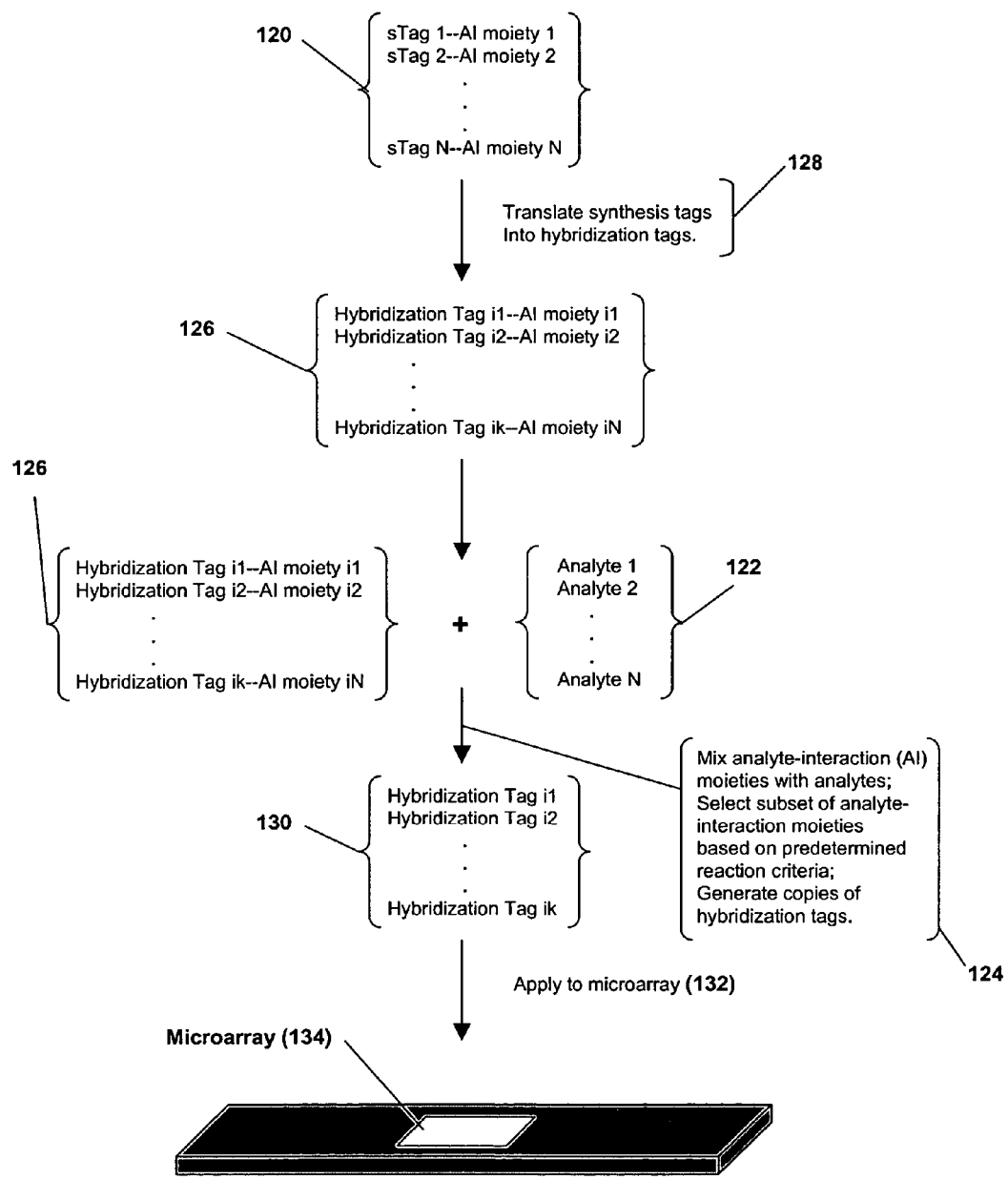
FIG. 1B diagrammatically illustrates the method of analyzing a plurality of polynucleotide analytes in accordance with one aspect of the invention in which synthesis tags are decoded prior to a multiplexed analytical reaction.

General schemes at the method and system of the invention are illustrated in FIGS. 1A and 1B. In accordance with one aspect of the invention, a set of analyte interaction ("A1") moieties each labeled with a unique synthesis tag ("sTag")(100) are combined with a set at analytes (102). A subset of analyte interaction moieties (106) are selected (104) based on predetermined criteria, e.g. binding strength, formation of a perfectly matched duplex between the analyte and analyte interaction moiety, after which the synthesis tags of the analyte interaction moieties are converted (108) to hybridization tags (110) and released from the analyte interaction moiety. After labeling the hybridization tags are applied (112) to a solid phase support preferably a microarray (114), having complements of the hybridization tags attached at addressable sites. In this way, there is a one-to-one correspondence between each synthesis tag and a unique hybridization tag and each hybridization tag and a site on a solid phase support having a known location, or an identifiable location depending on the methodology used for addressing the complements of the hybridization tags. For example, solid phase supports comprising microbeads may be addressed using optical signals and a readout may be obtained using flaw cytometric analysis.

In another and preferred aspect of the invention, a stock regent of analyte interaction moieties labeled with hybridization tags is produced prior to reaction with analytes, as illustrated in FIG. 1B. In this embodiment, analyte interaction moieties labeled with synthesis has (120) are produced as above. However, prior to carrying out any analyses, the set of synthesis tags are converted, or translated (128), into their corresponding hybridization tags to give a set of analyte interaction moieties labeled with hybridization tag (126). This then becomes a stock reagent for making measurements on a particular set of analytes. In particular, for polynucleotide analytes, such as genome fragments used in genotyping, the analyte interaction moieties are oligonucleotide probes. Thus, the reagents may be maintained and coped in a polymerase chain reaction (PCR) amplicon, or in a cloning vector library. Such reagents are then used as described above and illustrated in FIG. 1B; namely analyte interaction moieties labeled with hybridization tags (126) are combined with analytes (122), after which a subset of analyte interaction moieties is selected (124) according to predetermined criteria. Hybridization tags (130) are then released from the selected subset, copied, labeled, and applied (132) to microarray (134) or other suitable solid phase support.

Figure 2A:
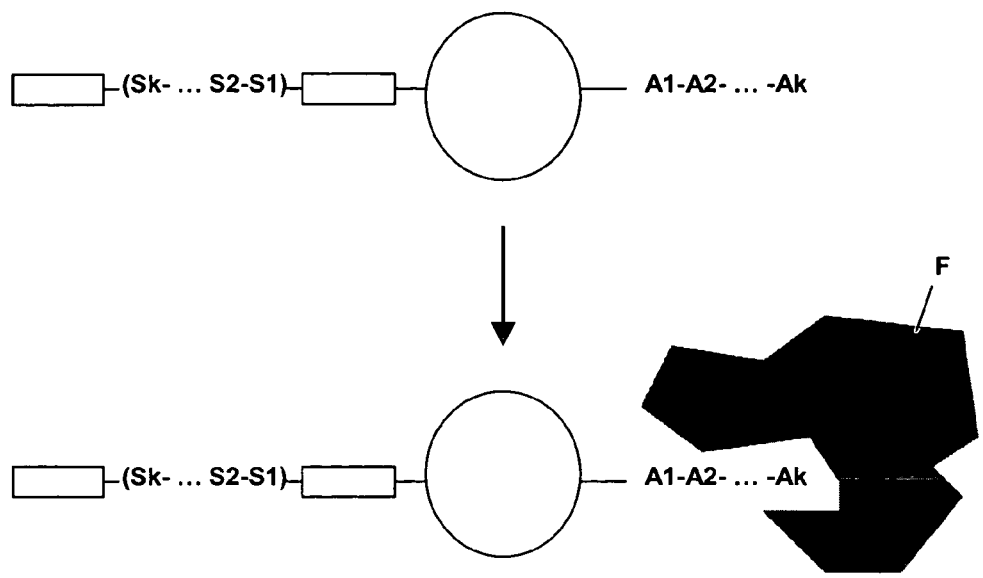
FIG. 2A illustrates an analyte interaction moiety and its tag for analyzing molecules that bind to members of a combinatorial library of linear polymers, such as peptides.

An analyte interaction moiety can be virtually any molecular structure that is either directly or indirectly attached to a synthesis tag or a hybridization tag that interacts with an analyte in such a way as to allow physical or chemical selection according to one or more predetermined criteria. Preferably, the interaction is a covalent or non-covalent binding reaction that allows selection of a subset of analyte interaction moieties based on the strength or stability of the conjugation. Analyte interaction moieties may be organic molecules, reactive groups, peptides, nucleic acids, or other molecules. Analyte interaction moieties may also be peptides or polypeptides expressed by phage display techniques, e.g. Barbas et al, editors. Phage Display: A Laboratory Manual (Cold Spring Harbor Laboratory, 2001). Preferably, analyte interaction moieties may are synthesized by microarray fabrication techniques in order to facilitate efficient large-scale production. In one aspect, an analyte interaction moiety may be attached to a synthesis tag indirectly as illustrated in FIG. 2A. Synthesis tag, "$S_K \sim \ldots S_2 \sim S_1$," and analyte interaction moiety, "$A1 \sim A2 \sim \ldots \sim A_x$," are synthesized on the same solid phase synthesis support using techniques as disclosed in Dower et al, U.S. Pat. No. 5,770,358; or Lerner Kim and Brenner. U.S. Pat. No. 6,060,596, which are incorporated by reference. Analyte interaction moiety FIG. 2A consists of a peptide having amino acid sequence "A1, A2, . . . Ak;" however, it could also consist of any compound capable of being synthesized on the support along with a synthesis tag. Although in FIG. 2A, the synthesis tag is exemplified with the same number of subunits the as analyte interaction moiety, this is not a necessary feature of the invention. In this embodiment, the analyte interaction moiety binds to the analyte, such as a receptor protein, antibody, or the like, and is selected, for example, by a capture moiety, which may be an affinity tag such as biotin, digoxigenin, dinitrophenol, or the like, or which may be a signal generating moiety, such as a colorimetric or fluorescent molecule, that would facilitate separation, for example, by fluorescence activated cell sorting (FACS). After selection, copies of the synthesis tag may be generated by amplification by PCR using primer binding sites. Preferably, copies of the synthesis tag are generated by extending a primer annealed to either site, i.e. by linear PCR, after which the copies are separated from the synthesis support, converted to hybridization tags, labeled, and applied to a microarray for a readout.

Figure 2B:
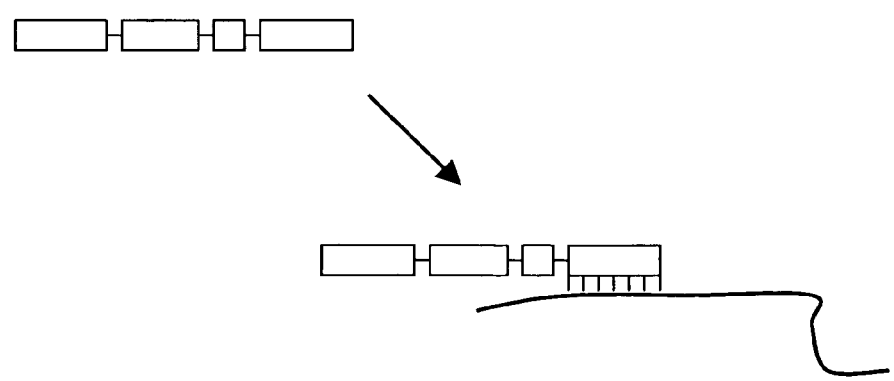
FIG. 2B illustrates an analyte interaction moiety and its tag for analyzing polynucleotide analytes by way of a hybridization reaction and/or a polymerase extension reaction.

Preferably, as illustrated in FIG. 2B, the analyte interaction moiety is an oligonucleotide probe or primer designed to form a perfectly matched duplex or triplex with a predetermined site on a target polynucleotide. Upon formation of such perfectly matched duplex or triplex, an analyte interaction moiety may be selected based on the stability of the triplex or duplex, or further reactions can be implemented, either for obtaining information about the target polynucleotide or for providing an alternative means for selection. For example, when an analyte interaction moiety forms a perfectly matched duplex with a target polynucleotide, it may be extended with a DNA polymerase in the presence of one or more labeled deoxynucleotide triphosphates using conventional protocols to determine the identity of the base immediately adjacent to the perfectly match duplex, e.g., as described in Fan et al, Genome Research, 10: 853-860 (2000); Hirsebbom et al, Proc. Natl. Acad. Sci., 97: 12164-12169 (2000); or the like.

A preferred analytical reagent of the invention for genotyping comprises analyte interaction moiety that is an oligonucleotide probe or primer designed to form a perfectly matched duplex or triplex with a predetermined site on a target polynucleotide, cleavage site, a hybridization or synthesis tag, and a primer binding site, As described more fully below, the primer binding site and the cleavage site provide a means for generating copies of labeled hybridization tags for application to a microarray after analyte interaction moiety is selected. Preferably, cleavage site is a cleavage site of a restriction endonuclease.

Virtually any population of polynucleotides may be analyzed by the method of the invention, including restriction digests, libraries of genomic fragments, cDNAs, mRNAs, or the like. Preferably, populations of polynucleotides analyzed by the invention are genomes of organisms whose sequences are known. Such genomes may be from any organism, including plant, animal, bacteria, or the like. When genomic DNA is obtained for medical or diagnostic use, it may be obtained from a wide variety of sources, including tissue biopsies, blood samples, amniotic cells, and the like. Genomic DNA is extracted from such tissues by conventional techniques, e.g. as disclosed in Berger and Kimmel, Editors, Methods in Enzymology, Vol. 152, Guide to Molecular Cloning Techniques (Academic Press, New York, 1987), or the like.

Hybridization Tags

An important feature of the invention is the use of hybridization tags consisting of oligonucleotides selected from a minimally cross-hybridizing set of oligonucleotides, or assembled from oligonucleotide subunits, i.e. "words," selected from a minimally cross-hybridizing set of oligonucleotides. Construction of such minimally cross-hybridizing sets are disclosed in Brenner et al, U.S. Pat. No. 5,846,719, and Brenner et al, Proc. Natl. Acad. Sci., 97: 1665-1670 (2000), which references are incorporated by reference. The sequences of oligonucleotides of a minimally cross-hybridizing set differ from the sequences of every other member of the same set by at least two nucleotides. Thus, each member of such a set cannot form a duplex (or triplex) with the complement of any other member with less than two mismatches. Preferably, perfectly matched duplexes of tags and tag complements of the same minimally cross-hybridizing set have approximately the same stability, especially as measured by melting temperature and/or dissociation temperature. Complements of hybridization tags, referred to herein as "tag complements," may comprise natural nucleotides or non-natural nucleotide analogs. Hybridization tags when used with their corresponding tag complements provide a means of enhancing the specificity, or discrimination, of hybridization.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides, such set having a maximum size of 332, when constructed as disclosed in Brenner et al, International patent application PCT/US96/09513. Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$, or 729, 12-mers.

When synthesized combinatorially, a hybridization tag preferably consists of a plurality of subunits, each subunit consisting of an oligonucleotide of 3 to 9 nucleotides in length wherein each subunit is selected from the same minimally cross-hybridizing set. In such embodiments, the number of hybridization tags available depends on the number of subunits per tag and on the length of the subunits.

Comma-Less Hybridization Tags

In one aspect of the invention, oligonucleotide tags are hybridized to their complementary sequences, or "anti-tags," which are attached to a solid phase support, such as a microarray. In such circumstances, it is desirable to employ oligonucleotide tags that are highly specific for anti-tags that form perfectly matched duplexes between each and every word of the tag, and that form, at best, only weakly stable duplexes with anti-tags in which words are not perfectly aligned. That is, in order to avoid spurious signals, it is desirable select sets of words (and tags constructed from them) that do not form stable duplexes when hybridized in an imperfectly aligned configuration, e.g. shifted 1 to 2, or more, bases out of perfect alignment. Sets of words with such properties may be constructed in several ways, including by inserting "commas" between words or by using words that inherently possess the above properties, i.e. which result in so-called "comma-less" tags , as discussed below. Tags of word having commas are readily constructed from the minimally cross-hybridizing sets of words disclosed by Brenner in the several references cited above. Either comma-containing or comma-less tags may be used with the invention; however, comma-less tags are preferred, as they generate the maximum degree of instability in a duplex formed after any small (e.g. 1-3 nucleotide) shift of the tag and anti-tag out of perfect alignment, also sometimes referred to herein as a "change of phase."

Figure 3A:
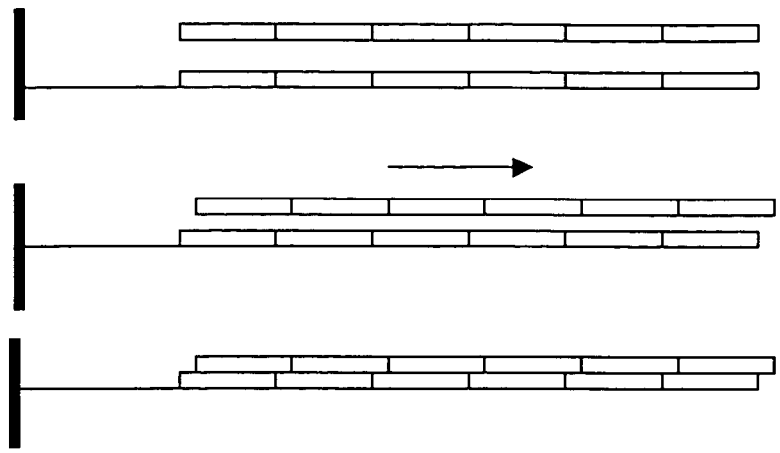
FIGS. 3A-3D illustrate hybridization tags with "commas" and a hybridization tag with the "comma-less" property.

As mentioned above, in tags synthesized combinatorially from shorter oligonucleotide "words" stable duplexes may font between a tag and its complement, even though the "words" are not perfectly aligned. As illustrated in FIG. 3A, an oligonucleotide tag consisting of words may align perfectly with its complement to form a perfectly matched duplex. However, with some selections of words, there may be other tags in the same repertoire that also form stabled duplexes, even though the tag is shifted, or out of alignment, by one or more bases with a complement. The stability of such spurious pairings is very close to that of the perfectly aligned pairings, making it difficult to discriminate between correctly hybridized tags and incorrectly hybridized tags.

Figure 3B:
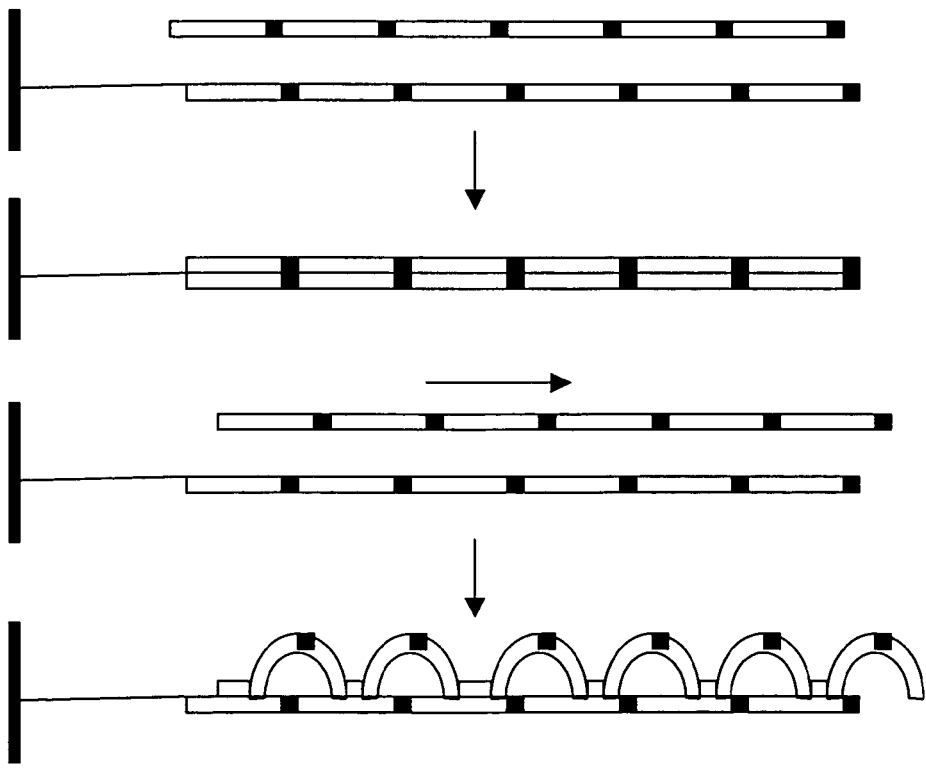

Such spurious hybridizations can be eliminated by designing tags that have large numbers of mismatches whenever the tag and its complement are shifted one or more bases away from the perfectly aligned configuration. As mentioned above, such designs can be accomplished by either introducing "commas" between words, or by designing words that inherently have the property that any shift out of perfect alignment introduces large numbers of stability-destroying mismatches. In its simplest form, "commas" may be one or more nucleotides introduced between the words of a tag, as illustrated in FIG. 3B. For example, the commas of a tag may consist of G's, while the words may consist of only A's, T's, and C's. Thus, for perfectly marched duplex to form (i) the commas must be aligned, and (ii) the words of a tag must each be the complement of the words of its anti-tag. If neither of these conditions is met, then no duplex will form, or if it does form, its stability will be vastly lower than that of the perfectly aligned and matched tags.

Figure 3C:
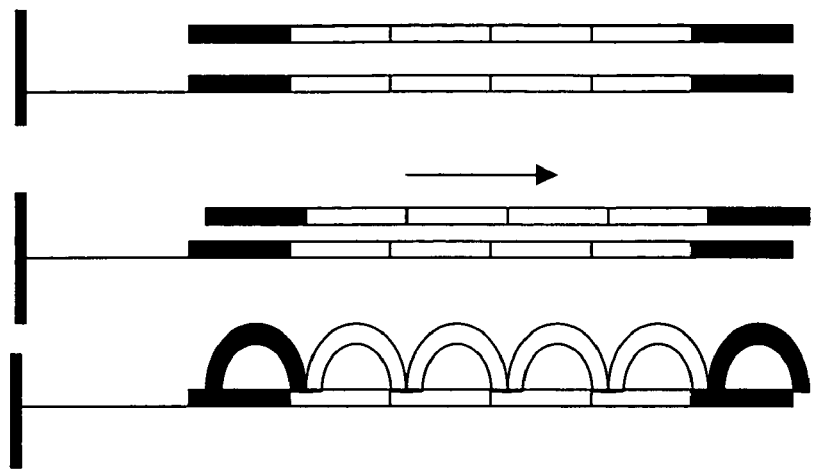

"Commas" may also take the form of words, as illustrated in FIG. 3C. Again, by way of example, the end words (shown in black) may consist of G's, whereas the internal words (shown in white) may consist of A's, C's, and T's. This constrains a tag and its complement to be correctly aligned. As above, absence perfect alignment, the stability of any duplex that forms will be vastly lower than that of a perfectly aligned tag and its complement.

Figure 3D:
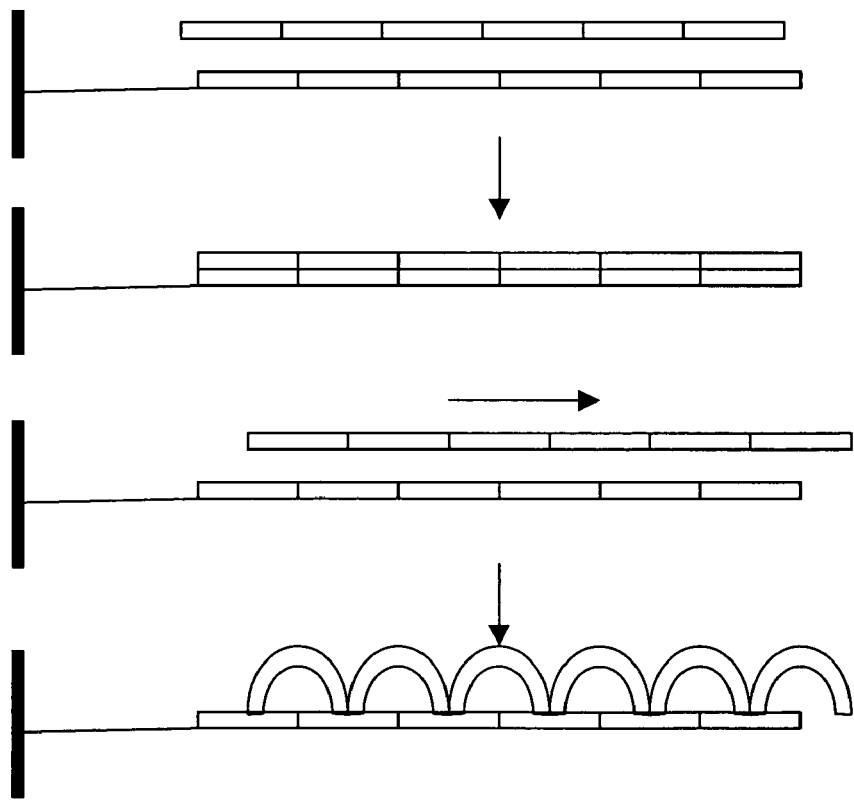

Finally, repertoires of tags without commas may be constructed from words that have the same properties as tags with commas. Such tags with the "comma-less" property are illustrated in FIG. 3D. That is, in order to form a perfectly matched duplex between a tag and a complement, the two must be perfectly aligned. Words for a repertoire of comma-less tags may be constructed in a wide variety of lengths, e.g. such words may have lengths in the range of from 4 to 10 nucleotides, and may consist of natural or non-natural nucleotides. In one aspect, words are construct from the four natural nucleotides, A, C, G, and T, whenever the resulting tags are operated on by enzymes. In another aspect, words may be constructed from nucleotides selected from the group consisting of A, C, G, T, and I, when the resulting tags (or anti-tags) are not processed by enzymes. Anti-tags synthesized on a solid phase support may typically be constructed from a wider variety of nucleotides than tags that are processed by enzymes. In one aspect of the invention, comma-less tags may be constructed from the following words.

Consider doublets of the four natural bases. Four sets of such doublets, 16 in all, can be defined as follows.

| I | II | III | IV |
|---|---|---|---|
| GT | CT | AT | AA |
| TG | TC | TA | TT |
| AC | AG | CG | CC |
| CA | GA | GC | GG |

In each set, all four differ in both positions from all the other members of the set, but when the four different sets are compared with each other, one base is held in common with one member of the other set. For example, in set I, eight different words can be created by combining doublets from set I with doublets from set II in the I-II order and the II-I order. Since each of these sets contain doublets that are the reverse complements of the other, the combinations are made such that none of I-II four-base words are the inverse complements of the II-I four-base words. Thus, if the I-II words are selected as follows: GTCT, TGTC, ACAG, and CAGA, then the II-I words can be defined only as follows:

| AGCA | or | AGGT |
|---|---|---|
| GAAC | | GATG |
| CTTG | | CTAC |
| TCGT | | TCCA | an arrangement which conserves the constraint that the members of each set differs by three bases from any member of the same set. From the above sets, several sets of words for comma-less tags can be constructed. Taking the first two sets, an "A" to the end of each words of the first set, and a "T" to the end of each word of the second set to give the following:

| AGCAT | GTCTA |
|---|---|
| GAACT | TGTCA |
| CTTGT | ACAGA |
| TCGTT | CAGAA |

Although the same process does not work with sets III and IV above because in III the doublets are self-complementary, further sets of words can be created by switching the I-II into II-I and vice versa, and adding the bases as above, which gives:

| CTGTA | CAAGT |
|---|---|
| TCTGA | ACGAT |
| AGACA | TGCTT |
| GACAA | GTTCT |

For tags not used in enzymatic processing, such as anti-tags synthesized on a solid phase support, the following sets employing deoxyinosine may be employed:

| AICAT | GTCTA |
|---|---|
| GAACT | TGTCA |
| CTTGT | ACAGA |
| TCITT | CAGAA | and

| CTGTA | CAAGT |
|---|---|
| TCTGA | ACIAT |
| AGACA | TICTT |
| GACAA | GTTCT |

Further sets of words for constructing comma-less tags are listed in FIG. 4.

Tag Complements Hybridization and Readout

Preferably, tag complements are synthesized on the surface of a solid phase support, such as a microscopic bead or a specific location on an array of synthesis locations on a single support, such that populations of identical, or substantially identical, sequences are produced in specific regions. That is, the surface of each support, in the case of a bead, or of each region, in the case of an array, is derivatized by copies of only one type of tag complement having a particular sequence. The population of such beads or regions contains a repertoire of tag complements each with distinct sequences. As used herein in reference to hybridization tags, tag complements, and synthesis tags, the term "repertoire" means the total number of different tags or tag complements in a given set or population.

Solid phase supports containing tag complements may take a variety of forms, e.g. particulate, single-piece and planar, such as a glass slide, and may be composed of a variety of materials, e.g. glass, plastic, silicon, polystyrene, or the like. Particulate solid phase supports include microspheres, particularly fluorescently labeled microspheres, e.g. Han et al, Nature Biotechnology, 19: 631-635 (2001); Kettman et al, Cytometry, 33: 234-243 (1998); and the like. Preferably, hybridization tags are detected by hybridizing them to their complementary sequences on a conventional microarray. Such microarrays may be manufactured by several alternative techniques, such as photo-lithographic optical methods, e.g. Pirrung et al, U.S. Pat. No. 5,143,854, Fodor et al, U.S. Pat. Nos. 5,800,992; 5,445,934; and 5,744,305; fluid channel-delivery methods, e.g. Southern et al, Nucleic Acids Research, 20: 1675-1678 and 1679-1684 (1992); Matson et al, U.S. Pat. No. 5,429,807, and Coassin et al, U.S. Pat. Nos. 5,583,211 and 5,554,501; spotting methods using functionalized oligonucleotides, e.g. Ghosh et al, U.S. Pat. No. 5,663,242; and Bahl et al, U.S. Pat. No. 5,215,882; droplet delivery methods, e.g. Caren et al, U.S. Pat. No. 6,323,043; Hughes et al, Nature Biotechnology, 19: 342-347 (2001); and the like. The above patents disclosing the synthesis of spatially addressable microarrays of oligonucleotides are hereby incorporated by reference. Preferably, microarrays used with the invention contain from 100 to 500,000 hybridization sites; more preferably, they contain from 200 to 250,000 hybridization sites; still more preferably, they contain from 500 to 40,000 hybridization sites; and most preferably, they contain from 500 to 32,000 hybridization sites.

Guidance for selecting conditions and materials for applying labeled oligonucleotide probes to microarrays may be found in the literature, e.g. Wetmur, Crit. Rev. Biochem. Mol. Biol., 26: 227-259 (1991); DeRisi et al, Science, 278: 680-686 (1997); Wang et al, Science, 280: 1077-1082 (1998); Duggan et al, Nature Genetics, 21: 10-14 (1999); Schena, Editor, Microarrays: A Practical Approach (IRL Press, Washington, 2000); Hughes et al (cited above); Fan et al, Genomics Research, 10: 853-860 (2000); and like references. These references are hereby incorporated by reference. Typically, application of hybridization tags to a solid phase support includes three steps: treatment with a pre-hybridization buffer, treatment with a hybridization buffer that includes the probes, and washing under stringent conditions. A pre-hybridization step is employed to suppress potential sites for non-specific binding of probe. Preferably, pre-hybridization and hybridization buffers have a salt concentration of between about 0.8-1.2 M and a pH between about 7.0 and 8.3. Preferably, a pre-hybridization buffer comprises one or more blocking agents such as Denhardt's solution, heparin, fragmented denature salmon sperm DNA, bovine serum albumin (BSA), SDS or other detergent, and the like. An exemplary pre-hybridization buffer comprises 6×SSC (or 6×SSPE), 5× Denhardt's solution, 0.5% SDS, and 100 µg/ml denatured, fragmented salmon sperm DNA, or an equivalent defined-sequence nucleic acid. Another exemplary pre-hybridization buffer comprises 6×-SSPE-T (0.9 M NaCl, 60 mM NaH2PO4, 6 mM EDTA (pH 7.4), 0.005% Triton X-100) and 0.5 mg/ml BSA. Pre-hybridization and hybridization buffers may also contain organic solvents, such as formamide to control stringency, tetramethylammonium chloride to negate base-specific effects, and the like. An exemplary hybridization buffer is SSPE-T and the desired concentration of isostringency probe. After hybridization, unbound and non-specifically bound isostringency probe is removed by washing the detection support under stringent conditions. Preferably, stringency of the wash solution is controlled by temperature, organic solvent concentration, or salt concentration. More preferably, the stringency of the wash conditions are determined to be about 2-5° C. below the melting temperature of the isostringency probes at the salt concentration and pH of the wash solution. Preferably, the salt concentration of the wash solution is between about 0.01 to 0.1 M.

Instruments for measuring optical signals, especially fluorescent signals, from labeled tags hybridized to targets on a microarray are described in the following references which are incorporated by reference: Stern et al, PCT publication WO 95/22058; Resnick et al, U.S. Pat. No. 4,125,828; Karnaukhov et al, U.S. Pat. No. 354,114; Trulson et al, U.S. Pat. No. 5,578,832; Pallas et al, PCT publication WO 98/53300; Brenner et al, Nature Biotechnology, 18: 630-634 (2000); and the like.

When tag complements are attached to or synthesized on microbeads, a wide variety of solid phase materials may be used with the invention, including microbeads made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11-147, vol. 44 (Academic Press, New York, 1976); U.S. Pat. Nos. 4,678,814; 4,413,070; and 4,046;720; and Pon, Chapter 19, in Agrawal, editor, Methods in Molecular Biology, Vol. 20, (Humana Press, Totowa, N.J., 1993). Microbead supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Generally, the size and shape of a microbead is not critical; however, microbeads in the size range of a few, e.g. 1-2, to several hundred, e.g. 200-1000 µm diameter are preferable, as they facilitate the construction and manipulation of large repertoires of oligonucleotide tags with minimal reagent and sample usage. Preferably, glycidal methacrylate (GMA) beads available from Bangs Laboratories (Carmel, Ind.) are used as microbeads in the invention. Such microbeads are useful in a variety of sizes and are available with a variety of linkage groups for synthesizing tags and/or tag complements.

Synthesis Code

One aspect of the invention is the production of the following oligonucleotide reagent for making measurements on polynucleotides, such as genomic fragments:

| 5'- | RNA Polymerase Site | Hybridization Tag | RS | Probe Sequence | -3' | where "RS" is a restriction site for removing the probe sequence prior to hybridization to remove extraneous polynucleotides from the hybridization reaction. The probe sequence is designed to have a sufficient length and composition to form stable duplexes with a target fragment so that a detection reaction can take place, e.g. a polymerase extension reaction (where the probe acts as a primer). The probe sequence may have a length in the range of from 12 to 36 nucleotides, or more usually, in the range of from 18 to 25 nucleotides. In one aspect, the above oligonucleotide reagent is constructed from the following type of reagent, which is synthesized on a microarray:

| 3'- | "B" primer | Synthesis Tag | Probe Sequence | RS | "T" primer | -5' | where the "B" primer is so-named because it is basal to, or at the base of, the oligonucleotide reagent with respect to the solid phase support, and the "T" primer is so-named because it is distal to the solid phase support, or at the "top" of the oligonucleotide. In the procedure for converting synthesis tags into hybridization tag each of the T primers and B primers will require a restrictions site that can be masked, e.g. by methylation. In one aspect, the need for such an restriction enzyme may be satisfied by Sfa NI (New England Biolabs, Beverly, Mass.), whose site may be blocked by replicating the sequence containing the site using primers containing the sequence, $GC^{Me}ATC$, where "$C^{Me}$" denotes a 5-methylcytosine. (Such primers are referred to herein as "m-B primers" and "m-T primers").

In one form, a synthesis tag of the invention is a concatenation of several two-nucleotide words (referred to herein as the "synthesis code" or "synthesis words") selected from a defined set. Since part of the process of converting synthesis tags into hybridization tags employs ligation at both ends of an adaptor, the ends must not be self-complementary. Thus, in selecting the two-word "code" for the synthesis tags, self-complementary sequences are excluded. After such exclusion, the remaining twelve two-nucleotide words can be grouped into two sets of six each:

| I | II |
|---|---|
| GG | CC |
| AA | TT |
| GA | TC |
| AG | CT |
| AC | GT |
| CA | TG |

Selecting the first four dimers from each of I and II, the code is RR and YY (where R is G or A, and Y is C or T). Another enzyme that is used in the construction is a type IIs restriction endonuclease that generates a two-base 5' overhang, such as Fau I (recognition sequence 5'-CCCGC(4/6)).

As explained more fully below, the synthesis words are converted into longer hybridization words using a so-called error-correcting synthesis procedure similar to that disclosed in Brenner and Williams, International patent publication, WO 00/20639, which is incorporated by reference.

Hybridization Code

In one aspect, hybridization codes of the invention consist of five bases and are assembled into hybridization tags following a procedure similar to that described in Brenner and Williams (cited above). Using synthesis tags, hybridization tags are constructed that are complements of the anti-tags attached to solid phase supports, such as microarrays. Such tags have the following form (SEQ ID NO: 1):

$$\ldots \underline{\text{GCATC}}\text{NNNNN-H}_1\text{-H}_2\text{-NNNNNNNNN}\underline{\text{CATCC}} \ldots \quad \text{(I)}$$
$$\text{Sfa NI} \qquad\qquad\qquad\qquad \text{Fok I}$$

Using an eight-word set described above, 64 such di-words are constructed, cloned in conventional vectors, and the DNA can be obtained thereafter by PCR. These reagents containing pairs of hybridization "words" are used to form word-pair conversion adaptors, described more fully below.

The principle of successively adding words is as follows. Assuming a word is in place ("$H_1$") and that a successive word is to be added. Since the previous word can be any of the eight words, then the material to be added will need to have all possibilities in the next position, call this "$H_2$", and there would be eight such sets. Thus, when the Sfa NI site is cut we will have the following end:

$$pZ_1Z_1Z_1Z_1 \; Z_1Z_0Z_0Z_0Z_0 \ldots \quad \text{(II)}$$
$$Z_1Z_0Z_0Z_0Z_0Z_0 \ldots$$

where the "$Z_1$'s" are the nucleotides of the added word, the "$Z_0$'s" are the nucleotides of the previous word, and "p" is a phosphate group. The new word is added by cutting the di-words of formula (I) at the Fok I site to give (SEQ ID NO: 2):

$$\ldots \text{GCATCNNNNN-}Z_2Z_2Z_2Z_2Z_2Z_2Z_2$$
$$\ldots \text{CGTAGNNNNN-}Z_2Z_2Z_2Z_2Z_2Z_2Z_2Z_xZ_xZ_xZ_xp$$

where the "$Z_2$'s" are the nucleotides of the next word, and the "$Z_x$'s" are the nucleotides of all the possible cleavage products. The cleavage product includes ends complementary to all of the possible ends of the cleavage product of formula (II). Thus, ligation of the two products permits combinatorial synthesis of the tags.

Production of Synthesis Tag-Probe Conjugates

Conversion of synthesis tags to hybridization tags is illustrated below for a system of about 4000 tags; thus, the system may be implemented by synthesis of the initial reagents on a microarray having 4000 discrete addressable sites. One of ordinary skill in the art recognizes that the illustrated system is readily expanded to include reagents of higher complexities by using larger microarrays. For example, microarrays having from 1 to 128 thousand addressable sites may be used with the invention; in another aspect, microarrays having from 1 to 64 thousand addressable sites may be used with the invention; and in still another aspect, microarrays having from 1 to 32 thousand addressable sites may be used with the invention.

Figure 5A:
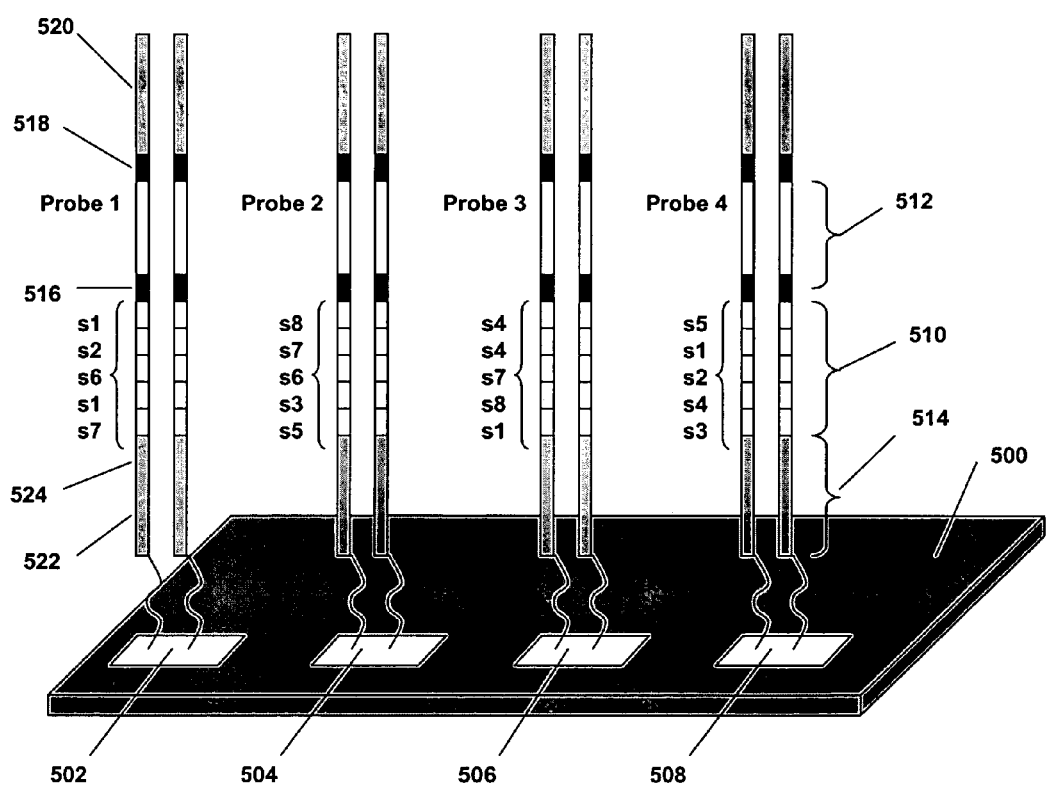
FIGS. 5A-5B illustrate synthesis of mixtures of oligonucleotides for use as reagents in large-scale analyses using microarray fabrication techniques.

A microarray is produced having oligonucleotides attached as shown in FIG. 5A. In this figure, for the sake of simplicity, only four different kinds of oligonucleotides are shown linked to solid phase support (500). In this embodiment, the different kinds of oligonucleotides are located at different addressable sites (502-508), and differ in sequence only in synthesis tag region (510) and probe region (512). Particular "words" are shown in the figure making up the synthesis tags, for example "$s_7s_1s_6s_2s_1$" at site (502); however, these are for illustration only. Generally, each oligonucleotide comprises the following elements, from proximal to distal with respect to the solid phase support: base primer binding site (514) which includes first restriction site (522) and second restriction site (524), sequence tag (510), third restriction site (516), probe sequence (512), and top primer binding site (520) which includes fourth restriction site (518). When the oligonucleotides of the microarray is synthesized, the identity of the synthesis tag at a given site is correlated with the identity of the probe sequence at the same site, so that a data set is formed for each microarray includes the identification of each synthesis tag and probe at each addressable site. In one aspect, a unique synthesis tag is associated with each different probe. In another aspect, each probe of a different addressable site on a microarray is associated with a different synthesis tag. Preferably, the oligonucleotides on the microarrays are as short as possible consistent with other design constraints in order to minimize synthesis errors. In one aspect, base primer binding site (514) may have a length in the range of from 12 to 30 nucleotides, or in a range of from 14 to 18 nucleotides. Synthesis tag (510) may have a length in the range of from 8 to 16 nucleotides; preferably, comprising from 4 to 8 two-nucleotide synthesis code words. Probes (512) may have a length in the range of from 8 to 36 nucleotides, or in the range of from 12 to 25 nucleotides. Top primer binding site (520) may have a length within the same ranges as those of the base primer. In way of a more particular example, the oligonucleotides may be constructed as follows starting from the 3' end of the base primer binding site:

3'-17 nucleotide base primer binding site,
8 nucleotide synthesis tag (four words of doublet code),
25 nucleotide probe sequence,
17 nucleotide top primer binding site
(including a Tsp 509 I site (5'-TTTAA) adjacent to the probe sequence)-5'

Second restriction site (518), exemplified by Tsp 509 I, is used to sever the probe sequence from the associated tag (before or after conversion depending on whether conversion takes place before or after probes interact with a sample containing target analytes).

In one embodiment, base primer (514) may have the structure (SEQ ID NO: 3):

. . . <u>GCATC</u>NNN<u>CCCGC</u>NNNN-$S_xS_xS_xS_x$-
    Sfa NI   Fau I where the underlined portions correspond to a Sfa NI site (5'-GCATC) and a Fau I site (5'-CCCGC), the "N"s are arbitrarily selected nucleotides, and the "$S_x$'s" are words of the synthesis code.

Figure 5B:
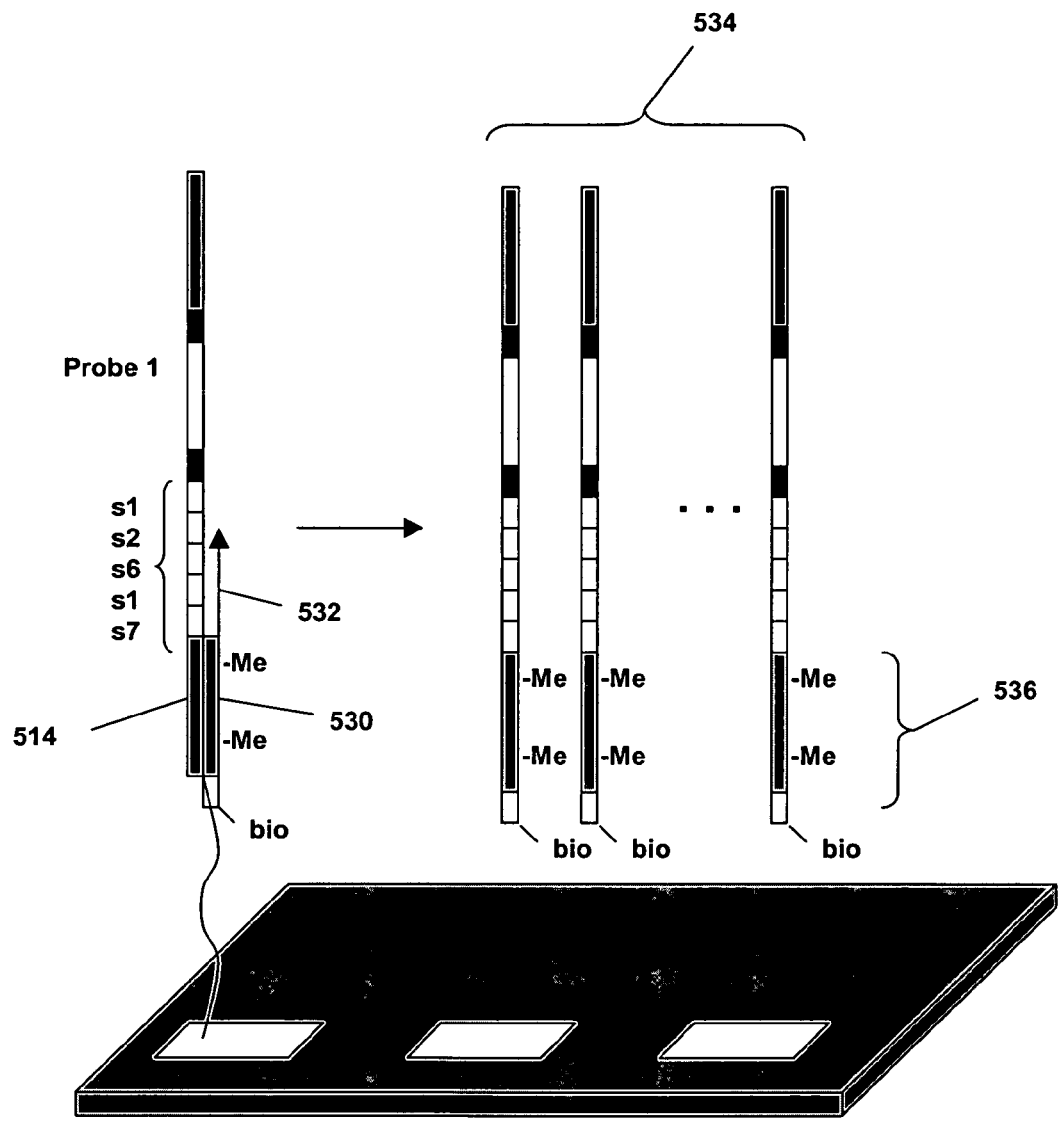

After the microarray is synthesized, multiple copies of complements of the attached oligonucleotides are produced as shown in FIG. 5B by linear amplification. Briefly, base primer (530) is annealed to base primer binding site (514) and extended (532), e.g. using a nucleic acid polymerase, such as a DNA polymerase, to produce complements (534). At this stage, base primer (530) may be selected with a 5' overhang so that the complementary base primmer sites (536) may be longer, e.g. 25 nucleotides, may contain cleavage-resistant nucleotides, such as 5-methyldexoycytosines, and capture moieties, such as biotin (which is indicated by "b" in FIG. 5B). After such copying, complements (534) are amplified using a top primer which contains a methylated Sfa NI site and which is also extended 2-7 nucleotides for added stability and specificity. PCR amplification does no introduce sequence biases under these circumstances, as the target sequences are all the same length. The product of this amplification, or amplicon, is referred to herein as the "microarray amplicon."

Converting the Synthesis Code to a Hybridization Code

An embodiment for converting a synthesis code to a hybridization code is described below. The process uses several reagents referred to collectively as "conversion reagents." Conversion reagents include cleavage adaptors, selection adaptors, quencher adaptors, initial conversion adaptors, and word-pair conversion adaptors, which are disclosed below for the particular case of two-nucleotide synthesis words and five-nucleotide hybridization words. One of ordinary skill in the art would recognize that the specific instructions for the embodiment below are readily applicable to more general embodiments.

The microarray amplicon described above is cut with Sfa NI which only cleaves the base primer sequence, as the Sfa NI site in the top primer sequence is protected with methylated cytosines. This gives products of the following form (SEQ ID NO: 4):

```
biotin-NN . . . GCATCNNNCC            pCGCANNN-S₁S₂S₃ . . .
       NN . . . CGTAGNNNGGGCᴹᵉGTp          NNN-S₁S₂S₃ . . .
```

The cleaved adaptor on the lefthand side is removed by capturing it with avidin or streptavidin, e.g. using Dynabeads (Dynal). To the remaining fragment the following cleavage adaptor is ligated:

```
biotin-NN . . . ACC
       NN . . . TGGGCGTp
``` to give the following (SEQ ID NO: 5):

```
biotin-NN . . . ACCCGCANNN-S₁S₂S₃ . . .
```

-continued

NN . . . TGGGCGTNNN-$S_1S_2S_3$ . . .

This is then cut with Fau I to cleave the above product to give the following:

$pS_1S_2S_3S_4$ . . .         (III)

$S_3S_4$ . . .

Any unligated adaptors, uncleaved products, and cleaved adaptors are removed by avidin or streptavidin as above.

In present embodiment, the terminal word, Si, will be one of the following set:

pGG . . .        pCC . . .

pGA . . .        pTC . . .

pAG . . .        pCT . . .

pAA . . .        pTT . . .

The object of the next set of steps is to purify aliquots of fragments having each of the eight ends shown above. Product (III) from above is divided into 8 tubes labeled 1 to 8. In each tube, all the sequences not corresponding to a selected end will be eliminated as follows. First, dideoxynucleotides are incorporated into the ends according to the following table in conventional extension reactions.

| Tube | End | Dideoxy's Used | | |
|---|---|---|---|---|
| 1 | pGG |   | T | G | A |
| 2 | pAG |   | T | G | A |
| 3 | pAA | C |   | G | A |
| 4 | pGA | C |   | G | A |
| 5 | pCC | C | T |   | A |
| 6 | pTC | C | T |   | A |
| 7 | pTT | C | T | G |   |
| 8 | pCT | C | T | G |   |

After extension, a second selection is carried out in each tube by carrying out ligation reactions with two types of adaptors, referred to herein as "selection" adaptors and "quencher" adaptors.

Selection adaptors have the following structure (SEQ ID NO: 6):

5'-      . . . GCATCNNNCCCGCNN

AAAA . . . CGTAGNNNGGGCGNNK$_1$K$_2$p   (3' overhang)

Where $K_1$ and $K_2$ are synthesis words. A quencher adaptor has a sequence of 20 nucleotides (for example) terminating as follows (SEQ ID NO: 7):

5'-AAANNNNNNNNNNNNNNNNNN

NNNNNNNNNNNNNNNNNNNK$_1$K$_2$p

As explained below, a sequence of reactions are carried out to select for ends as shown in the following table:

| Tube | $X_1X_2$ | Selection | Quencher $K_1K_2$ | Code Word Selected |
|---|---|---|---|---|
| 1 | GG & AG | CC | TC | GG |
| 2 | GG & AG | TC | CC | AG |
| 3 | AA & GA | TT | CT | AA |
| 4 | AA & GA | CT | TT | GA |
| 5 | CC & TC | GG | AG | CC |
| 6 | CC & TC | AG | GG | TC |
| 7 | TT & CT | AA | GA | TT |
| 8 | TT & CT | GA | AA | CT |

In each of the eight tubes, there will be three kinds of templates present after completion of the ligation reations: "capped" (A), "selected" (B), and "quenched" (C), having the structures shown below:

(A)      $pS_1S_2$ . . .

<$S_2$ . . .

where "<$S_2$" indicates that the sequence is "capped" by the incorporation of a dideoxynucleotide.

(SEQ ID NO: 8)
(B)   5'-    N . . . GCATCNNNCCCGCNNS$_1$S$_2$ . . .

AAAAN . . . CGTAGNNNGGGCGNNK$_1$K$_2$ . . .

(SEQ ID NO: 9)
(C)   5'-AAANNNNNNNNNNNNNNNNNNNNNS$_1$S$_2$ . . .

NNNNNNNNNNNNNNNNNNNNNNNK$_1$K$_2$ . . .

The reaction mixtures of each tube are then treated with exonuclease III. The capped and quenched templates are reduced to 5' half molecules, as they are not protected from exonuclease digestion. The selected templates have their lower strands protected; thus, they will survive as a single strand (SEQ ID NO: 10):

3'-AAAAN . . . CGTAGNNNGGGCGNNK$_1$K$_2$ . . . . -5'

Note that the top primer sequence is protected by use of methylated cytosines. Such protection is now switched to the base primer by carrying out linear amplification using a primer of the form (SEQ ID NO: 11):

5'-TTTTN . . . GC$^{Me}$ATCNNNCCCGCAA

After such linear amplification, double stranded material in the tubes is destroyed with exonuclease III treatment and the remaining templates in each tube are amplified by PCR using the following primers:

Methylated base primer:
5'- . . . GC$^{Me}$ATCNNNCCCGCAA          (SEQ ID NO: 11)

Top primer:
3'-        AAAAA<u>CTAGC</u> . . . -biotin  (SEQ ID NO: 12)

where the underlined sequence is a Sfa NI recognition site. After amplification, amplicons are digested with Sfa NI and removal of unused primer, cleaved adaptors, and uncleaved template is carried out with streptavidinated or avidinated magnetic beads, or like technique. This leaves the following end on the templates:.

```
        3'- . . . NTTTAp -5'

5'- . . . N
```

Next, to each tube add under ligation conditions "starter" words incorporated in the following initial conversion adaptor (SEQ ID NO: 13):

```
       H₂AAAAACTAC^MeG . . . N*N*N*N*N -5'
5'-pAAATH₁TTTTTGATG      C . . . N
``` where $H_i$ is a 5-nucleotide hybridization "word" (or its complement), and *N is a nucleotide having a nuclease-resistant intra-nucleoside linkage, such as a phosphorothioate linkage.

From this point, depending on whether it is desired to keep the individual probe sequences in a combinatorial mixture or separate, the reaction mixtures of the tubes are mixed, or are kept separate. If it were only desired to deconvolve them, without labeling them, there would be no need to use the tag adaptors, but only a common one. In this aspect of the invention, a combinatorial mixture is desired so the contents of all of the tubes are mixed, and unligated strands are destroyed by treating with T7 exonuclease 6, which gives single stranded products of the form:

```
3'-[Base primer] . . . TTAA[word][Methylated top primer]-5'
```

This product is amplified with the following primers:

```
                                      (SEQ ID NO: 14)
5'-biotin-N . . . GCATCAACCCGCAA -5'   Base primer (SEQ ID NO: 15)
3'-AAAAACTAC^MeG . . . N               Top primer
```

At this point, the set of steps from the beginning of this section may be re-started, except that instead of the initial conversion adaptor, word-pair conversion adaptors, as shown earlier, would be used. This will result in the classification of each of the sequences in the synthesis, i.e. the synthesis code, into whatever code is required for use. The cycles of conversion are continued until the last step where a slightly different procedure is followed. The last step of the conversion is carried out as follows. First, the sequence is cleaved exactly at the probe beginning. This is incorporated directly at the last step by changing the selector templates to the following (SEQ ID NO: 16):

```
       [Base primer] . . . GCATCAAAAAAA

. . . CGTAGTTTTTTTK₁K₂
``` where $K_1$ and $K_2$ are defined as described above. This will do the de-coding and when the GCATC is cut it will leave the probe sequence exactly at the 3' end. Alternatively, Mn1 I could be used in the base primer to give selectors as follows (SEQ ID NO: 17):

```
       [Base primer]       . . . CCTCAAAA

. . . GGAGTTTTK₁K₂
```

When this is cleaved, it will result in a ⅞ overhang and again the probe sequences terminate at exactly the correct end.

As above, when the last word is converted a special set of adaptors is used. Instead of the top primer, a T7 RNA polymerase site is employed as (or within) a primer, such as shown below (SEQ ID NO: 18):

```
       5'-pNNNNH_j TGATCACTCAGCATAAT-3'

H_j ACTAGTGAGTCGTATTA
``` where $H_j$ is the final word of a hybridization tag (or its complement). After ligation, the product is amplified using the following primers:

```
              5'-NN . . . CCTCAAAA-3'
```

3'-[T7 RNA polymerase recognition site] CC-biotin

After PCR, the amplicon is cleaved with Mn1 I, denatured, and captured with avidin or streptavidin to give:

3'-[probe sequence]TTAA[T7 RNA polymerase recognition site]

Application to Genotyping

The reagents produced by the above methods may be used for genotyping, either where probes are joined to tags of the invention, or where tags are used directly. In both cases, sequences are chosen, e.g. 25 nucleotides in length, which can act as primers and terminate just before a polymorphic site. In the first case, a microarray would be synthesized having a primer, or probe, sequence and synthesis tag at each site in the following form:

[T7 RNA polymerase site][tag][RS][primer/probe]

In the second case, there is no tag sequence, so the following sequence would have the form:

[T7 RNA polymerase site][primer/probe]

In both cases, a sample is digested with a restriction endonuclease, such as Dpn I, cleaving at GATC, and leaving four-nucleotide 5' overhangs:

```
         5'-pGATC------------------

------------------CTAGp-5'
```

Next, dideoxyG is incorporated to terminate the strands:

```
         5'-pGATC------------------G>

<G------------------CTAGp-5'
``` where "<G" and "G>" represent the dideoxyG in the two strands. After such extension, a primer is ligated to the ends, referred to herein as the "X primer," which is similar in composition to the primer containing the RNA polymerase site, and which has a 5' overhang of CTA to give:

where "<" and ">" indicate nicks in the duplex cause by the dideoxynucleosides. Denaturing of the strands gives the following single strands:

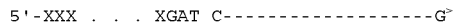

These are annealed with a large excess of the above reagents to give:

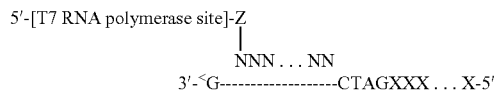

where Z is a tag or a conventional phosphate linkage when no tag is present. Note that the X primer sequence cannot be primed until it is copied, which is why the original strands are terminated with dideoxyG.

The primers are extended to give (SEQ ID NO: 19):

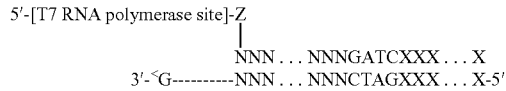

after which the mixture is digested with exonuclease I to remove the single stranded DNA with the free 3'-end. This gives the following:

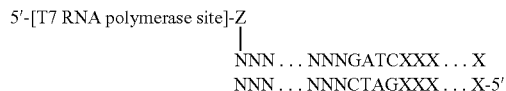

which is treated with a DNA polymerase in the presence of the four dNTPs to generate the following duplex:

This can be done either by PCR with X primers protected on 5' ends by phosphorothioates and then destroying with T7 exo 6 after an initial PCR to amplify the material, destroy all single stranded material and excess primer with exo I followed by a further linear amplification with X primer only.

Now templates may be sorted according to the identity of the bases in the position adjacent to the primer. The above reagent is employed, except that a T7 polymerase site is used that is 3 bases short on its 5' end and carries a biotin. After performing the selection, four tubes are obtained containing the primer annealed to the template and protected from exonuclease III digestion by the appropriate phosphorothioates. The templates may be released after capture, and a product is amplified using T7 polymerase and X primers. In the case where tags are employed, the sequence is cleaved at the restriction site and then the tags are copied using T7 polymerase. In the second case where the primer is its own tag, the sequence is cut at the GATC site, e.g. with Dpn II to remove the X primer and copy the extended tag which does not introduce extraneous DNA onto a microarray for a readout.

In the second case, the following alternative may also be used. At the stage where a strand is linearly amplified using an X primer, a biotin-labeled X primer is used. Sorting is then preformed as before, with unlabeled primer. That is, the original reagent is used again with a T7 polymerase site that is short three bases, as described above. After treating with exonuclease III to perform the selection, the sequence is treated with exonuclease I to remove all single stranded DNA from the 3' end. This includes unprotected template and excess primers. Templates protected by undegraded primers may now be removed. Such primers have the following structure:

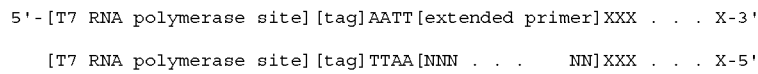

The selected material can be amplified with T7 RNA polymerase and X primers, in such a way as to produce an excess of strands with the following polarity:

5'-[T7 RNA polymerase site][primer]sX

[T7 RNA polymerase site][primer][template]-biotin-5'

This is copied directly with T7 RNA polymerase so that only the primer is linearly amplified and labeled for application to a microarray of complementary sequences for a readout.

---

I claim:

1. A system for detecting one or more properties of each of a plurality of analytes, the system comprising:
   a first set of analyte-interaction nucleic acid moieties capable of reacting with the plurality of analytes under assay reaction conditions, each analyte-interaction nucleic acid moiety having a synthesis tag comprising a concatenation of words;
   conversion reagents for converting each synthesis tag into a hybridization tag and for releasing the hybridization tag from the analyte-interaction nucleic acid moieties, wherein the hybridization tag comprises one or more words determined by a corresponding synthesis tag, each word of the hybridization tag being longer than each word of its corresponding synthesis tag; and
   a solid phase detection array for detecting the released hybridization tags, thereby detecting the one or more properties of each of the plurality of analytes.

2. The system of claim 1 wherein each of said words of said hybridization tag is selected from a minimally cross-hybridizing set, each word of the minimally cross-hybridizing set being an oligonucleotide having a length in the range of from three to nine nucleotides and differing in nucleotide sequence from every other word of such set by at least two nucleotides.

3. The system of claim 2 wherein said hybridization tag is comma-less.

4. The system of claim 3 wherein said analyte-interaction moiety is an oligonucleotide.

5. The system of claim 4 wherein said words of said hybridization tag each have a length in the range of from 4 to 5 nucleotides, wherein said words of said synthesis tag have a length of two nucleotides, and wherein said solid phase detection array is a microarray having from 100 to 100,000 hybridization sites.

6. A solid phase support having attached a plurality of tag complements, the solid phase support comprising:
   a plurality of addressable sites, each addressable site having copies of only one tag complement, the tag complement having the structure:

$W_1W_2...W_n$ wherein each $W_i$ for i=1, 2, ... n is selected from a group of oligonucleotides having nucleotide sequences:

| | |
|---|---|
| AICAT | GTCTA |
| GAACT | TGTCA |
| CTTGT | ACAGA |
| TCITT | CAGAA | or

| | |
|---|---|
| CTGTA | CAAGT |
| TCTGA | ACIAT |
| AGACA | TICTT |
| GACAA | GTTCT. |

* * * * *

SEQUENCE LISTING

```
<160> NUMBER OF SEQ ID NOS: 19

<210> SEQ ID NO 1
<211> LENGTH: 33
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (6)..(28)
<223> OTHER INFORMATION: n is a, c, g, or t

<400> SEQUENCE: 1
gcatcnnnnn nnnnnnnnnn nnnnnnnnca tcc                               33

<210> SEQ ID NO 2
<211> LENGTH: 16
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (6)..(16)
<223> OTHER INFORMATION: n is a, c, g, or t

<400> SEQUENCE: 2
gcatcnnnnn nnnnnn                                                  16

<210> SEQ ID NO 3
<211> LENGTH: 25
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (14)..(25)
<223> OTHER INFORMATION: n is a, c, g, or t

<400> SEQUENCE: 3
gcatcnnncc cgcnnnnnnn nnnnn                                        25

<210> SEQ ID NO 4
<211> LENGTH: 9
<212> TYPE: DNA
<213> ORGANISM: Artificial
<220> FEATURE:
<223> OTHER INFORMATION: Adaptor
<220> FEATURE:
<221> NAME/KEY: misc_feature
<222> LOCATION: (6)..(7)
<223> OTHER INFORMATION: n is a, c, g, or t
```

```
<400> SEQUENCE: 4 gcatcnncc                                                              9

<210> SEQ ID NO 5
<211> LENGTH: 16
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (8)..(16)
<223> OTHER INFORMATION: n is a, c, g, or t

<400> SEQUENCE: 5
acccgcannn nnnnnn                                                     16

<210> SEQ ID NO 6
<211> LENGTH: 15
<212> TYPE: DNA
<213> ORGANISM: Artificial
<220> FEATURE:
<223> OTHER INFORMATION: Adaptor
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t

<400> SEQUENCE: 6
gcatcnnncc cgcnn                                                      15

<210> SEQ ID NO 7
<211> LENGTH: 23
<212> TYPE: DNA
<213> ORGANISM: Artificial
<220> FEATURE:
<223> OTHER INFORMATION: Adaptor
<220> FEATURE:
<221> NAME/KEY: misc_feature
<222> LOCATION: (4)..(23)
<223> OTHER INFORMATION: n is a, c, g, or t

<400> SEQUENCE: 7
aaannnnnnn nnnnnnnnnn nnn                                             23

<210> SEQ ID NO 8
<211> LENGTH: 18
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (13)..(18)
<223> OTHER INFORMATION: n is a, c, g, or t

<400> SEQUENCE: 8
gcatcnnncc ccnnnnnn                                                   18

<210> SEQ ID NO 9
<211> LENGTH: 18
```

```
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (13)..(18)
<223> OTHER INFORMATION: n is a, c, g, or t

<400> SEQUENCE: 9
gcatcnnncc ccnnnnnn                                                 18

<210> SEQ ID NO 10
<211> LENGTH: 19
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (6)..(8)
<223> OTHER INFORMATION: n is a, c, g, or t
<220> FEATURE:
<221> NAME/KEY: misc_feature
<222> LOCATION: (14)..(19)
<223> OTHER INFORMATION: n is a, c, g, or t

<400> SEQUENCE: 10
cgtagnnngg gcgnnnnnn                                                19

<210> SEQ ID NO 11
<211> LENGTH: 15
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(8)
<223> OTHER INFORMATION: n is a, c, g, or t

<400> SEQUENCE: 11
gcatcnnncc cgcaa                                                    15

<210> SEQ ID NO 12
<211> LENGTH: 10
<212> TYPE: DNA
<213> ORGANISM: Artificial
<220> FEATURE:
<223> OTHER INFORMATION: Primer

<400> SEQUENCE: 12
cgatcaaaaa                                                          10

<210> SEQ ID NO 13
<211> LENGTH: 15
<212> TYPE: DNA
<213> ORGANISM: Artificial
<220> FEATURE:
<223> OTHER INFORMATION: Adaptor
<220> FEATURE:
<221> NAME/KEY: misc_feature
<222> LOCATION: (11)..(15)
<223> OTHER INFORMATION: n is a, c, g, or t

<400> SEQUENCE: 13
```

```
gcatcaaaaa nnnnn                                                    15

<210> SEQ ID NO 14
<211> LENGTH: 14
<212> TYPE: DNA
<213> ORGANISM: Artificial
<220> FEATURE:
<223> OTHER INFORMATION: Primer

<400> SEQUENCE: 14
aacgcccaac tacg                                                     14

<210> SEQ ID NO 15
<211> LENGTH: 10
<212> TYPE: DNA
<213> ORGANISM: Artificial
<220> FEATURE:
<223> OTHER INFORMATION: Primer

<400> SEQUENCE: 15
gcatcaaaaa                                                          10

<210> SEQ ID NO 16
<211> LENGTH: 12
<212> TYPE: DNA
<213> ORGANISM: Artificial
<220> FEATURE:
<223> OTHER INFORMATION: Adaptor

<400> SEQUENCE: 16
gcatcaaaaa aa                                                       12

<210> SEQ ID NO 17
<211> LENGTH: 12
<212> TYPE: DNA
<213> ORGANISM: Artificial
<220> FEATURE:
<223> OTHER INFORMATION: Adaptor
<220> FEATURE:
<221> NAME/KEY: misc_feature
<222> LOCATION: (1)..(4)
<223> OTHER INFORMATION: n is a, c, g, or t

<400> SEQUENCE: 17
nnnnttttga gg                                                       12

<210> SEQ ID NO 18
<211> LENGTH: 26
<212> TYPE: DNA
<213> ORGANISM: Artificial
<220> FEATURE:
<223> OTHER INFORMATION: Adaptor
<220> FEATURE:
<221> NAME/KEY: misc_feature
<222> LOCATION: (1)..(9)
<223> OTHER INFORMATION: n is a, c, g, or t

<400> SEQUENCE: 18
nnnnnnnnnt gatcactcag cataat                                        26

<210> SEQ ID NO 19
<211> LENGTH: 10
<212> TYPE: DNA
<213> ORGANISM: Artificial
<220> FEATURE:
<223> OTHER INFORMATION: Primer
<220> FEATURE:
<221> NAME/KEY: misc_feature
```

```
<222> LOCATION: (1)..(3)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 19 nnngatcnnn                                                          10
```